US00PP12128P2

(12) United States Plant Patent
Zary

(10) Patent No.: US PP12,128 P2
(45) Date of Patent: Oct. 9, 2001

(54) FLORIBUNDA ROSE PLANT NAMED 'JACZOTTA'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/400,368

(22) Filed: Sep. 21, 1999

(51) Int. Cl.[7] ..... A01H 5/00
(52) U.S. Cl. ..... Plt./142
(58) Field of Search ..... Plt./141, 142, 143, Plt./130, 131, 132

*Primary Examiner*—Howard J. Locker
(74) *Attorney, Agent, or Firm*—Klarquist Sparkman Campbell Leigh & Whinston, LLP

(57) ABSTRACT

Floribunda rose plant having a high centered bud and open flower form; vigorous, upright, well-branched plant; glossy, dark green foliage; and novel, pink and yellow flower.

1 Drawing Sheet

The present invention relates to a new and distinct variety of rose plant of the floribunda class which was originated by me by crossing the variety 'JACient', (U.S. Plant Pat. No. 6,725), with an unnamed floribunda seedling (not patented).

The primary objective of this breeding was to produce a new rose variety having the high centered bud and half open flower form; the vigorous, well-branched plant; and the glossy, dark green foliage of the female parent; combined with the novel, pink and yellow flower color of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright, well-branched growth;
2. Dark green, glossy, disease resistant foliage;
3. Bright pink with light yellow reverse flowers; and
4. High centered buds and open flowers.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—'JACient' (U.S. Plant Pat. No. 6,725).

*Pollen parent.*—Unnamed floribunda seedling (not patented).

Classification:

*Botanical.*—*Rosa hybrida.*

*Commercial.*—Floribunda.

FLOWER

Observations made from specimens grown in a garden environment at Somis, Calif. from March 1998 to August 1999.

Blooming habit: Continuous.

Bud:

*Size.*—1½ inches long when the petals start to unfurl.

*Form.*—The bud form is long; pointed ovoid.

*Color.*—When sepals first divide, bud color is Red Group 46B where exposed to bright sunlight; otherwise, Red Group 46D. When half blown, the upper sides of the petals are Red Group 54A, except for near the petal base, where it is Yellow Group 7C; and the lower sides of the petals are Yellow Group 7D at the petal base, then becoming White Group 155B with a pink blush of Red Group 55D at the petal edge.

*Sepals.*—Color: Green Group 138B, becoming Greyed-Purple Group 183A when exposed to bright sun. Surface texture: Covered in fine hairs. There are three normally appendaged sepals. There are two unappendaged sepals with hairy edges.

*Receptacle.*—Color: Green Group 137A except when exposed to bright sun, then it is Greyed-Purple Group 183A. Shape: Funnel. Size: Medium (about ⅜ inch×¼"). Surface: Smooth.

*Peduncle.*—Length: Short (about 2 to 2½ inches). Surface: Smooth. Color: Yellow-Green Group 147B; except when exposed to bright sunlight, then it is Greyed-Purple Group 183A. Strength: Stiff; erect.

Bloom:

*Size.*—Large. Average open size is 4 to 4½ inches.

*Borne.*—Singly and several together in flat clusters of three to five blooms.

*Stems.*—Strength: Strong. Average length is about 14 to 18 inches.

*Form.*—When first open, bloom is high centered. Permanence: Retains its form to the end; outer petals curl back.

*Petalage.*—Number of petals under normal conditions: 30.

*Color.*—The upper sides of the petals are Red Group 54A, except near the petal base where it is Yellow Group 7C. The reverse sides of the petals are Yellow Group 7D at the petal base, becoming White Group 155B with a pink blush of Red Group 55D at the petal edge. The base of each petal has a Yellow Group 12A, ⅜ inch×⅜ inch half moon at the point of attachment on both petal surfaces. The major color on the upper side is Red Group 54A.

*Variegations.*—On some petals there is a small, cream colored streak along the mid-rib (Yellow-White Group 158D).

*Discoloration.*—The general tonality at the end of the first day: No change. At the end of the third day: No change. There is a general fading from Red Group 54A to Red Group 54C from day five to day seven when petal drop occurs.

*Fragrance.*—Slight.

Petals:

*Texture.*—Thick.

*Shape.*—Round.

*Form.*—Tips slightly recurved.

*Arrangement.*—Imbricated. There are no petaloids in the center.

*Persistence.*—Petals drop off cleanly before drying.

*Lastingness.*—On the plant: Fair (about six days). As a cut flower: Fair (about seven days).

Reproductive parts:

*Anthers.*—Size: Medium. Quantity: Many. Color: Yellow-Orange Group 20C. Arrangement: Regular around styles.

*Filaments.*—Color: Yellow-Orange Group 20B.

*Pollen.*—Present.

*Styles.*—Color: Red Group 49D.

*Stigmas.*—Color: Yellow-White Group 158A.

Plant:

*Form.*—Bush.

*Growth.*—Vigorous; upright; branching. At maturity, height is 40 to 44 inches, width is 32 to 36 inches.

Foliage: Number of leaflets on normal mid-stem leaves: Five or seven.

*Size.*—Medium (5 inches long×3½ inches wide).

*Quantity.*—Abundant.

*Color.*—New foliage: Upper and lower surfaces: Greyed-Purple Group 183A. Old foliage: Upper surface: Green Group 136A. Lower surface: Green Group 136C.

Leaflets:

*Shape.*—Pointed oval.

*Texture.*—Leathery; glossy.

*Edge.*—Serrated.

*Serration.*—Single; small.

*Petiole rachis.*—Color: Green Group 136A (upper); Yellow-Green Group 147B (lower).

*Petiole underside.*—Smooth, with occasional prickles.

*Stipules.*—Long (about ¾ to 1 inch); serrated; bearded.

*Disease resistance.*—Resistant to mildew and rust, susceptible to blackspot under normal growing conditions.

*New wood.*—Color: Greyed-Purple Group 187A. Bark: Smooth

*Old wood.*—Color: Green Group 137B. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 187A.

*Color when mature.*—Greyed-Orange Group 173D.

Small prickles:

*Quantity.*—On main stalks: None. On laterals: None.

I claim:

1. A new and distinct variety of rose plant of the floribunda class, substantially as herein shown and described, characterized particularly by its high centered bud and open flower form; vigorous, upright, well-branched plant; glossy, dark green foliage; and novel, pink and yellow flower.

* * * * *

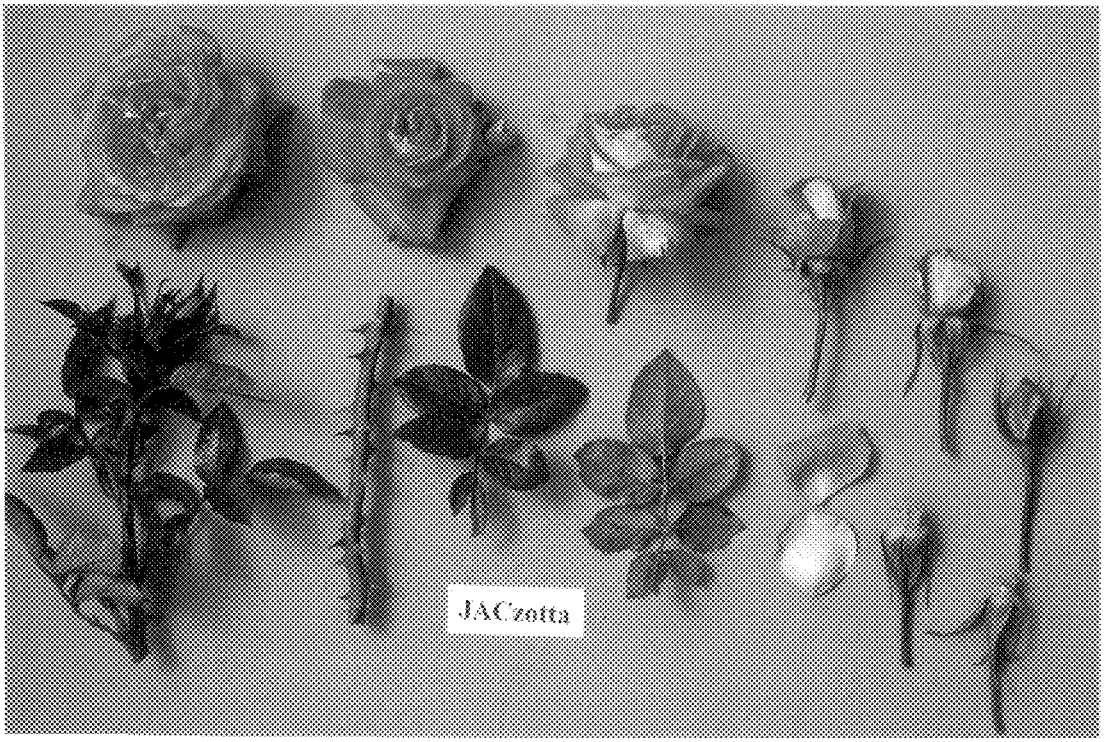
JACzetta